United States Patent [19]

Friedrich et al.

[11] Patent Number: 4,621,073
[45] Date of Patent: Nov. 4, 1986

[54] CYCLIC PEPTIDES HAVING SOMATOSTATIN ACTIVITY

[75] Inventors: Axel Friedrich, Frankfurt am Main; Wolfgang König; Volker Teetz, both of Hofheim am Taunus; Rolf Geiger, Frankfurt am Main; Jürgen K. Sandow, Königstein, all of Fed. Rep. of Germany

[73] Assignee: Hoechst Aktiengesellschaft, Fed. Rep. of Germany

[21] Appl. No.: 575,703

[22] Filed: Jan. 31, 1984

[30] Foreign Application Priority Data

Feb. 2, 1983 [DE] Fed. Rep. of Germany ........ 3303345

[51] Int. Cl.$^4$ .................... A61K 37/24; C07K 7/26
[52] U.S. Cl. ..............,.................... 514/11; 514/806; 530/311
[58] Field of Search .............. 260/112.5 R; 424/177; 514/11, 806; 530/311

[56] References Cited

U.S. PATENT DOCUMENTS 4,235,886 11/1980 Freidinger et al. .......... 260/112.5 R
4,303,583 12/1981 Kim et al. ................... 260/239.3 T
4,310,518 1/1982 Freidinger et al. .......... 260/112.5 R

OTHER PUBLICATIONS

Veber et al., *Nature*, 292, 55–58 (1981).

*Primary Examiner*—Delbert R. Phillips
*Attorney, Agent, or Firm*—Finnegan, Henderson, Farabow, Garrett & Dunner

[57] ABSTRACT

The invention relates to cyclic hexapeptides of the general formula III

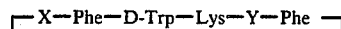

in which X represents the radical of an L-aminoacid of the general formula IIIa

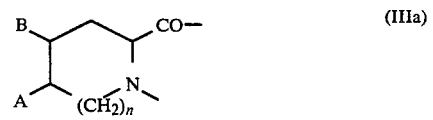

in which A and B are identical or different and denote alkyl having 1 to 3 carbon atoms, or A and B together represent a saturated, unsaturated or aromatic monocyclic or bicyclic structure having 3 to 6 carbon atoms, n denotes 0 or 1, and Y represents an aliphatic or aromatic L-aminoacid the side chain of which can be hydroxylated, and their salts with physiologically tolerated acids, and to a process for their preparation and their use and their intermediates.

19 Claims, No Drawings

CYCLIC PEPTIDES HAVING SOMATOSTATIN ACTIVITY

Somatostatin is a peptide comprising 14 aminoacids of the formula I

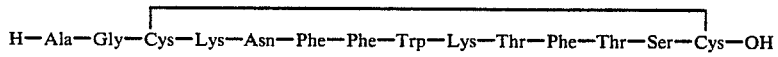

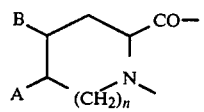

It is found in both the hypothalamus (Science 179, 77–79, 1973) and the gastrointestinal tract, such as, for example, in the D cells of the islets of the pancreas (Acta Physiol. Scand. Suppl. 473, 15, 1979). Somatostatin regulates, for example, the level of sugar in the blood by inhibiting insulin or glucagon, and it inhibits growth hormone, TSH, ACTH, prolactin, pancreozymin, secretin, motilin, VIP, GIP and, via gastrin, also gastric acid section (Am. J. Med. 70, 619–626, 1981). Having these properties, it would be possible for it to have a variety of uses as a therapeutic agent. It is possible to employ it for disturbances of the level of sugar in the blood (for example diabetes) via its inhibition of the secretion of insulin and glucagon. A raised level of GH in the plasma, which can induce, for example, acromegaly or psoriasis, is lowered by somatostatin. Due to its inibitory effect on gastrin, it lowers gastric acid and cures the syndromes produced by excess gastric acid, such as, for example, gastrointestinal bleeding. The growth of hormone-producing tumors which give rise to, for example, the Verner-Morrison syndrome (VIP-producing tumor) or the Zollinger-Ellison syndrome (gastrin-producing tumor) can be inhibited by somatostatin.

However, somatostatin is very readily metabolized and it is thus only worthwhile to administer it as an infusion. A search for somatostatin analogs which are more potent and have a longer action is justified to simplify therapy and reduce costs. A somatostatin analog which had greater activity was obtained by replacing Trp by D-Trp. It inhibits the secretion of growth hormone and insulin about 8 times more, and glucagon about 6 times more, than does somatostatin (Biochem. Biophys. Res. Commun. 65, 746-51, 1975). Even shortening to a cyclic hexapeptide of the formula II

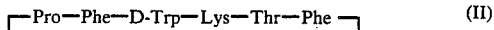

in which, in addition to D-Trp, a Phe is replaced by a Pro exhibits a strong and protracted somatostatin activity (Nature 292, 55-58, 1981)).

It has now been found that the somatostatin activity can be further increased by replacing the proline in formula II by more lipophilic heterocycles.

The invention relates to cyclic hexapeptides of the general formula III

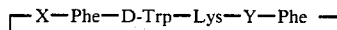

in which X represents the radical of a L-aminoacid of the general formula IIIa in which A and B are identical or different and denote alkyl having 1 to 3 carbon atoms, or A and B together represent a saturated, unsaturated or aromatic monocyclic or bicyclic structure having 3 to 6 carbon atoms, n denotes 0 or 1, and Y represents an aliphatic or aromatic L-aminoacid the side-chain of which can be hydroxylated, and their salts with physiologically tolerated acids.

The invention also relates to a process for the preparation of these compounds which comprises cyclizing, by known processes of peptide synthesis, linear hexapeptides of the general formula IV

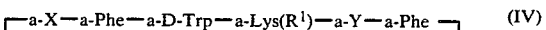

in which

X and Y have the abovementioned meanings, $R^1$ represents a protective group for the $\epsilon$-amino group, and in which five of the moieties a denote a chemical bond and one of the moieties a represents —OH+ H—, and then removing in a suitable manner protective groups which are present.

The abovementioned peptides of the formula IV are understood specifically to include the compounds of the formulae Iva–Ivf given below:

| | |
|---|---|
| H-X-Phe-D-Trp-Lys($R^1$)-Y-Phe-OH | (IVa) |
| H-PHe-X-Phe-D-Trp-Lys($R^1$)-Y-OH | (IVb) |
| H-Y-Phe-X-Phe-D-trp-Lys($R^1$)-OH | (IVc) |
| H-Lys($R^1$)-Y-Phe-X-Phe-D-Trp-OH | (IVd) |
| H-D-Trp-Lys($R^1$)-Y-Phe-X-Phe-OH | (IVe) |
| H-Phe-D-Trp-Lys($R^1$)-Y-Phe-X-OH | (IVf) | in which $R^1$, X and Y have the abovementioned meanings.

The invention also relates to linear hexapeptides of the general formula IV in which a, X, Y and $R^1$ have the abovementioned meanings, and to a process for their preparation which comprises subjecting esters of the formula IV, in which a, $R^1$, X and Y have the abovementioned meanings and in which five of the moieties a denote a chemical bond and one of the moieties a represents —OR+Z—, R denoting alkyl having 1-6 carbon atoms, preferably methyl, to alkaline hydrolysis and then removing the Z radical by hydrogenation.

The esters of the formula IV are understood specifically to include the compounds of the formula Va–Vf given below:

Z-X-Phe-D-Trp-Lys($R^1$)-Y-Phe-OR  (Va)

Z-Phe-X-Phe-D-Trp-Lys(R¹)-Y-OR  (Vb)

Z-Y-Phe-X-Phe-D-Trp-Lys(R¹)-OR  (Vc)

Z-Lys(R¹)-Y-Phe-X-Phe-D-Trp-OR  (Vd)

Z-D-Trp-Lys(R¹)-Y-Phe-X-Phe-OR  (Ve)

Z-Phe-D-Trp-Lys(R¹)-Y-Phe-X-OR  (Vf)

in which X, Y, R and R¹ have the abovementioned meanings. R¹ preferably represents Boc.

The synthesis of compounds of the formulae Va–Vf can be carried out either by the Merrifield solid phase method or by the classical route in solution. Standard processes are described in, for example, "The PeptidesAnalysis, Synthesis, Biology, vol. 1 Major Methods of Peptide Bond Formation, Part A", ed. E. Gross, J. Meierhofer, Academic Press N.J. (1979).

In the case of a cyclohexapeptide, there are six possibilities of cyclizing various chain peptides to give the same cyclopeptide. Since tryptophane tends to form by-products during said removal of protective groups (for example removal of the Boc group) in the solid phase method, in such cases it is advantageous to add tryptophane on as the last aminoacid. Using the solid phase method, hexapeptides which have, for example, the general formula VI H-D-Trp-Lys(Z)-Y-Phe-X-Phe-O-R²  (VI)

in which X and Y have the above meaning, and R² represents the solid phase resin, are prepared. The protective group used for the ε-amino group of lysine is a urethane protective group, preferably the benzyloxycarbonyl radical (Z). The β-hydroxyl group of threonine can remain unprotected.

The hexapeptide which is bonded to the resin via an ester group is removed using hydrazine. The corresponding hydrazide is produced and is cyclized, preferably after conversion into the azide. The protected cyclic peptides are purified by chromatography, during which diastereoisomers which are present are also removed. After removing the protective groups of the benzyl type by catalytic hydrogenation, the cyclopeptides according to the invention are obtained.

In classical peptide synthesis, the amino protective groups are, for example, the Z radical, which can be removed by catalytic hydrogenation, or the 9-fluorenylmethyloxycarbonyl radical (Fmoc), which can be removed by secondary amines, while the ε-amino group of lysine is preferably protected by the Boc radical. Peptides of the general formula Va-f are built up in steps.

The free acids are produced by alkaline hydrolysis of the esters (preferably OMe). The α-amino protective group is then removed, and the peptides which are unprotected at the N and C terminals are cyclized by the methods of peptide chemistry. The protected cyclic peptides are purified by chromatography. Tert.-butyl protective groups are preferably removed using trifluoroacetic acid, to which is added 1,2-dimercaptoethane.

Racemic aminoacids of the formula IIIb

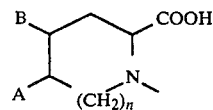

(IIIb)

in which A, B and n have the above meaning, are known from, for example, European Pat. A 50,800, European Pat. No. A 31,741, European Pat. No. A 51,020, European Pat. No. A 49,658, European Pat. No. A 49,605, European Pat. No. A 29,488, European Pat. No. A 46,953 and European Pat. No. A 52,870. Tetrahydroisoquinoline-3-carboxylic acid is described in J. Amer. Chem. Soc. 70 (1948) 182. Decahydroisoquinoline-3-carboxylic acid is known from European Pat. No. A 52,870, and 2,3-dihydro-[1H]-indole-2-carboxylic acid is known from U.S. Pat. No. 4,303,583. Cis,exo-octahydro-[1H]-indole-2-carboxylic acid, cis,exo-octahydro-2-cyclopenta[b]pyrrole-2-carboxylic acid and cis,exo-azabicyclo[5.3.0]-decane-3-carboxylic acid are, inter alia, the subject matter of German Patent Application No. P 3,151,690.4. German Patent Application No. P 3,226,768.1 relates to, inter alia, ciis,endo-octahydrocyclopenta[b]pyrrole-2-carboxylic acid, P 3,246,503.3 relates to, inter alia, cis,endo-azabicyclo[5.3.0]decane-3-carboxylic acid, No. P 3,210,496.0 relates to, inter alia, cis,endo- and cis,exo-2,3,3a,4,5,7a-hexahydro[1H]indole-2-carboxylic acid, No. P 3,300,774.8 (HOE 83/F 003) relates to, inter alia, diethylproline, and P 3,242,151.6 relates to, inter alia, 3-azatricyclo[5.2.1.0²,⁶]decane-4-carboxylic acid. Cis,endo-octahydro-[1H]-indole-2-L-carboxylic acid is known from European Patent A 37,231. A process for resolving the racemates of aminoacids of the formula IIIb is the subject matter of German Patent Application No. P 3303112.6 (HOE 83/F 016).

Examples of possible aminoacids Y are L-alanine, L-serine, L-threonine, L-valine, L-leucine, L-isoleucine, L-phenylalanine or L-tyrosine.

The customary NH₂ protective groups which are described in M. Bodanszky et al. in "Peptide Synthesis", 2nd edition (1976), John Wiley & Sons, can be used as the protective groups R¹. Alkanoyl having 1–6 carbon atoms, t-butoxycarbonyl and benzyloxycarbonyl are preferred.

The invention also relates to the use of the compounds of the formula III as medicines, to pharmaceutical products which contain these compounds, to processes for their preparation and to their use as medicines.

The peptides according to the invention have the inhibitory properties of somatostatin, but their duration of action is considerably longer at lower doses. For example, after intravenous administration to the rat, these peptides reduce gastric acid with an ED₅₀ of about 5 μg/kg. The reduction in gastric acid is maintained for 2 hours. In comparison, somatostatin in an i.v. dose of 30 μg/kg has no effect whatever on gastric acid. A reduction in gastric acid is only brought about by infusing somatostatin. The ED₅₀ for inhibition of growth hormone is likewise about 2–20 μg/kg i.v. In a test of the potentiation of the hypoglycemic effect of insulin in adrenalectomized rats, cyclo-(Aoc-Phe-D-Trp-Lys-Val-Phe), for example, showed an effect which was at least twice that of cyclo-(Pro-Phe-D-Trp-Lys-Thr-Phe). Even at a dose of 0.07 μg/kg⁻¹·min⁻¹, the Aoc analog significantly reduced blood glucose by up to 24%, while the Pro analog was completely ineffective at a dose of as much as 0.318 μg/kg$^{-1}$. min$^{-1}$. The new compounds can also be administered orally and intranasally. However, in these instances considerably higher doses are necessary because of the poorer absorption.

Because of their somatostatin-like activity, the new compounds can be employed in every instance where somatostatin infusions exhibit a favorable effect: for example for hemorrhage of the gastrointestinal tract, for gastric ulcers, for metabolic disturbances associated with raised levels of hormones which can be inhibited by somatostatin, such as, for example, conditions in which insulin and growth hormone in the plasma are too high, for acromegaly and psoriasis, for diabetes mellitus (inhibition of glucagon), and for states of shock.

An effective dose in humans is 0.1–10 μg/kg on parenteral administration and is about 1–100 μg/kg on intranasal administration. Since somatostatin does not inhibit administered exogenous insulin, a product combined with insulin is recommended for diabetes mellitus.

EXAMPLE 1

Preparation of the linear carrier-bound Boc-hexapeptides of the general formula Boc-D-Trp-Lys(Z)-Y-Phe-X-Phe-O-R 24 g of hydroxymethylated Merrifield resin is suspended in about 360 ml of CH$_2$Cl$_2$, and 15.9 g of Boc-Phe-OH, 12.4 g of dicyclohexylcarbodiimide and 7.4 g of 4-dimethylaminopyridine are added to the stirred suspension. Reaction is allowed to continue overnight for conversion to be as nearly quantitative as possible. The solid residue is filtered off and washed (1×50 ml of CH$_2$Cl$_2$, 4×50 ml of CH$_2$Cl$_2$/methanol 1:1 and 2×50 ml of CH$_2$Cl$_2$). OH groups on the resin which are not blocked are then occupied using 3 ml of benzoyl chloride in 200 ml of CH$_2$Cl$_2$ with 2.4 ml of pyridine as the base. A solid-phase synthesis is then carried out in the steps given below using 4 g of this resin which has been charged with Boc-Phe:

| Step | Number | Time (min.) | Volume (ml) | Reagents |
|---|---|---|---|---|
| 1 | 2 | 15 | 40 | 10% trifluoroacetic acid/ 0.5% methanesulfonic acid in CH$_2$Cl$_2$ |
| 2 | 2 | 4 | 50 | dioxane/CH$_2$Cl$_2$, 1:1 |
| 3 | 2 | 4 | 40 | CH$_2$Cl$_2$/methanol, 1:1 |
| 4 | 3 | 3 | 50 | CH$_2$Cl$_2$ |
| 5 | 3 | 5 | 50 | 10% diisopropylethylamine in CH$_2$Cl$_2$ |
| 6 | 5 | 3 | 50 | CH$_2$Cl$_2$ |
| 7 | 1 | 240 | 60 | CH$_2$Cl$_2$, 10 mmol Boc-aminoacid, 10 mmol dicyclohexylcarbodiimide, 10 mmol 1-hydroxybenzotriazole |
| 8 | 4 | 5 | 50 | CH$_2$Cl$_2$/MeOH 1:1 |
| 9 | 2 | 3 | 50 | CH$_2$Cl$_2$ |

The time stated for step 7 is usually exceeded since it is generally necessary to leave it to stand overnight. The completeness of coupling was checked after step 9 using picric acid or chloranil in toluene. After the last wash of stage 9, the loaded Merrifield resin was dried thoroughly by suction. Yield: between 5.9 and 6.2 g.

EXAMPLE 2

Preparation of the Boc-hexapeptide-hydrazides of the general formula Boc-D-Trp-Lys(Z)-Y-Phe-X-Phe-NH-NH$_2$ 6 g of carrier-bound peptide are suspended in 100 ml of DMF, 5 ml of absolute hydrazine hydrate are added and the mixture is allowed to stir at room temperature for 2 days. The residue is removed by suction, thoroughly washed with dimethylformamide and methanol, and the filtrate is evaporated to dryness. In order to remove excess hydrazine completely, methanol/toluene 1:1 is added to the residue several times and removed again in a rotary evaporator. The remaining residue is digested several times with a little water to remove benzoyl hydrazide, and is finally filtered off and dried over P$_2$O$_5$ under oil pump vacuum. The crude yields are between 1.0 and 2.2 g depending on the peptide. It was possible to purity the crude peptides by chromatography on silica gel (solvent: CH$_2$Cl$_2$/MeOH/HOAc 100:8:5).

EXAMPLE 3

Preparation of the hexapeptide-hydrazides of the general formula H-D-Trp-Lys(Z)-Y-Phe-X-Phe-NH-NH$_2$ 1 mmol of Boc-hexapeptide-hydrazide is substantially dissolved in about 200 ml of methanol, and 10 ml of 4N HCl in methanol are added. The mixture is stirred for about 15 min., excluding moisture, and then evaporated to dryness in a rotary evaporator. The hexapeptidehydrazide bishydrochlorides thus obtained are used immediately, without further characterization, in the next stage.

EXAMPLE 4

Cyclization to give compounds of the general formula

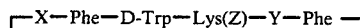

1 mmol of hexapeptide-hydrazide dihydrochloride is dissolved in 25 ml of DMF. 0.6 ml of 4N HCl in dioxane and then 0.18 ml of amyl nitrite are added to the stirred solution at −15° C. The reaction mixture is left at low temperature for about 40 min and then transferred into 2 liters of DMF which has been precooled to −20° C., and the mixture is neutralized with 0.81 ml of diisopropylethylamine. The total mixture is left at about 0° C. for 2 days, then allowed to reach room temperature and stirred for a further 3 days. The residue remaining after removal of the solvent in vacuo is dissolved in methanol H$_2$O 1:1 and stirred with about 800 mg of mixed bed ion exchanger for 24 hours. After filtering off the ion exchanger and evaporating the aqueous-methanolic phase, an amorphous residue remains and this is purified by semipreparative HPLC on silica gel (eluting agent: CH$_2$Cl$_2$ ethanol/acetic acid, 100:5:0.5).

EXAMPLE 5

Preparation of cyclopeptides of the general formula

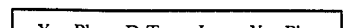

To remove the ε-Z protective group of lysine, the main fraction obtined from HPLC is dissolved in methanol and hydrogenated in the presence of a palladium catalyst for about 2 hours. After filtering off the catalyst, the filtrate is evaporated in vacuo and the residue is again chromatographed on silica gel (methylene chloride/methanol acetic acid/water, 70:30:1.5:6).

TABLE 1

Physical data for the Boc-hexapeptide-hydrazides

| | | Aminoacid analysis | | | | |
|---|---|---|---|---|---|---|
| X | Y | Phe | Lys | X | Y | $[\alpha]_D^{23}$ (c = 0.5 methanol) |
| Tic | Thr | 2.00 | 1.03 | 1.00 | 0.97 | −7.3° |
| Oic | Thr | 2.00 | 0.94 | 0.92 | 1.03 | −15.8° |
| Aoc | Thr | 1.99 | 0.97 | 1.00 | 1.04 | −11.1° |

TABLE 2

Characteristic NMR data (δ values) of the cyclic compound of the general formula ⌐X—Phe—D-Trp—Lys(Z)—Y—Phe⌐

| X | Y | d, 1H Indole-NH | d, 1H each Amide-NH | d, 1H Indole-CH | d, 1H —OH | s, 2H CH$_2$ (Z) | d, 3H CH$_3$ (Thr) |
|---|---|---|---|---|---|---|---|
| Tic | Thr | 10,72 | 8,60<br>8,59<br>8,38<br>7,80 | 7,54 | 5,18 | 5,0 | 1,08 |
| Oic | Thr | 10,80 | 8,78<br>8,52<br>8,08 | 7,63 | | 5,0 | 0,95 |
| Aoc | Thr | 10,70 | 8,58<br>8,38<br>8,30<br>7,79 | 7,47 | | 5,0 | 1,02 |

The final products of the general formula

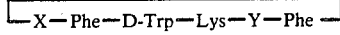

⌐X—Phe—D-Trp—Lys—Y—Phe⌐ show the same characteristic NMR data apart from lacking the signals for the benzyloxycarbonyl(Z) group.

Abbreviations

Tic=tetrahydroisoquinoline-3-carboxylic acid
Oic=cis,endo-octahydroindole-2-carboxylic acid
Aoc=cis-octahydrocyclopenta[b]pyrrole-2-endo-carboxylic 5 acid

EXAMPLE 6 cyclo-(Aoc-Phe-D-Trp-Lys-Val-Phe)

(a) Z-Phe-Aoc-OBzl 18.5 g of the salt of Z-Phe-OH and H-Aoc-OBzl are dissolved in 100 ml of dimethylformamide. 4.83 g of HOBt and 7.0 g of DCC are added to this solution at 0° C. The mixture is stirred at 0° C. for one hour and left to stand at room temperature overnight. Next day, the precipitate is filtered off with suction and the filtrate is evaporated. The residue is dissoled in ethyl acetate and extracted by shaking consecutively with water, saturated NaHCO$_3$ solution, 1N H$_2$SO$_4$, saturated NaHCO$_3$ solution and water. The ethyl acetate solution is dried over Na$_2$SO$_4$ and evaporated.

Yield: 16.1 g of an oil.

For purification, the product is chromatographed on silica gel using methylene chloride/methanol 9.7:0.3 (vol./vol.).

Yield: 15.4 g of a pale oil. TLC: one spot in methylene chloride/methanol (9.7:0.3).

(b) Z-Phe-Aoc-OH 14.5 ml of 2N NaOH are added to a solution of 15.4 g of Z-Phe-Aoc-OBzl in 60 ml of dioxane/water 8:2. The mixture is allowed to stand at room temperature for about 20 hours, and it is then neutralized with 1N H$_2$SO$_4$ and evaporated. The residue is taken up in water and the solution is acidified to pH 2-3 with 1N H$_2$SO$_4$. The oil which separates out is extracted with ethyl acetate, and the ethyl acetate solution is dried over Na$_2$SO$_4$ and evaporated.

Yield: 13.7 g of oil.

(c) Z-Phe-Aoc-Phe-OMe 4.02 ml of N-ethylmorpholine and 6.9 g of DCC are added to a solution of 13.7 g of Z-Phe-Aoc-OH, 6.77 g of H-Phe-OMe.HCl and 4.46 g of HOBt in 50 ml of dimethylformamide at 0° C. The mixture is stirred at 0° C. for one hour and left to stand at room temperature overnight. Working up is analogous to Example 6a.

Yield: 18.8 g of oil. After purification in analogy to 6a: 16.0 g of pale oil.

(d) H-Phe-Aoc-Phe-OMe.HCl 16.0 g of Z-Phe-Aoc-Phe-OMe are dissolved in methanol. A 10% Pd/charcoal catalyst is added and the mixture is hydrogenated using an autotitrator at pH 4.5. After hydrogenation is complete, the catalyst is removed by filtration through kieselguhr under suction, the filtrate is evaporated and the residue is triturated with diethyl ether. The precipitate is filtered off with suction and dried.

Yield: 8.67 g, melting point 79°-91° C., $[\alpha]_D^{23}$= +26.9° c=1, methanol).

(e) Z-Val-Phe-Aoc-Phe-OMe 1.03 ml of N-ethylmorpholine and 1.76 g of DCC are added to a solution of 4.0 g of H-Phe-Aoc-Phe-OMe.HCl, 2.016 g of Z-Val-OH and 1.14 g of HOBt in 30 ml of dimethylformamide at 0° C. The mixture is left to stand at 0° C. for one hour and then at room temperature overnight. The working up and purification are as in Example 6a.

Yield: 4.2 g of oil.

(f) H-Val-Phe-Aoc-Phe-OMe.HCl 4.95 g of Z-Val-Phe-Aoc-Phe-OMe are dissolved in methanol and catalytically hydrogenated as in d. Yield: 3.31 g (oily substance).

(g) Z-D-Trp-Lys(Boc)-OH 6.87 g of HOBt and 25 g of Z-D-Trp-OTcp are added to a suspension of 11.89 g of H-Lys(Boc)-OH in 100 ml of dimethylformamide. The mixture is stirred overnight and then evaporated. The residue is triturated with petroleum ether three times and subjected to countercurrent distribution between ethyl acetate and saturated NaHCO$_3$ in 3 stages. The ethyl acetate phases are combined, extracted by shaking with KHSO$_4$/K$_2$SO$_4$ solution, dried over Na$_2$SO$_4$ and evaporated.

Yield: 49.1 g of oil.

For further purification, the oil is chromatographed on 400 g of silica gel. Elution is first carried out with methylene chloride and then the substance is washed off with a mixture of methylene chloride/methanol water 16:4:0.3 (vol./vol.). The eluate is evaporated and dried under high vacuum.

Yield: 31.1 g of amorphous foam.

(h) Z-D-Trp-Lys(Boc)-Val-Phe-Aoc-Phe-OMe 0.7 ml of N-ethylmorpholine and 1.14 g of DCC are added to a solution of 3.31 g of H-Val-Phe-Aoc-Phe-OMe.HCl, 3.12 g of Z-D-Trp-Lys(Boc)-OH and 0.9 g of HOBt in 20 ml of dimethylformamide at 0° C. Working up is carried out in analogy to Example 6a.

Yield: 4.61 g, melting point 117°–119° C., $[\alpha]_D^{23} = -24.2°$ (c=1, methanol).

(i) Z-D-Trp-Lys(Boc)-Val-Phe-Aoc-Phe-OH 2.6 g of Z-D-Trp-Lys(Boc)-Val-Phe-Aoc-Phe-OMe are dissolved in 25 ml of dioxane/water (8:2). 5 ml of 1N NaOH are added to this solution and the mixture is allowed to stand at room temperature for 1.5 hours. It is then neutralized with 1N H$_2$SO$_4$ and the solution is evaporated. The residue is worked up in analogy to Example 6b.

Yield: 2.2 g, decomposition above 118° C., $[\alpha]_D^{23} = -25.9°$ (c=1, methanol).

(k) H-D-Trp-Lys(Boc)-Val-Phe-Aoc-Phe-OH 2.2 g of z-D-Trp-Lys(Boc)-Val-Phe-Aoc-Phe-OH are dissolved in 90 percent acetic acid and, after adding a Pd/charcoal catalyst, are hydrogenated. After hydrogenation is complete, the catalyst is filtered off with suction through a clarifying filter and the filtrate is evaporated. The residue is triturated with water. NaHCO$_3$ solution (a total of about 2.5 ml) is added with stirring to the suspension (pH 3.1) until a pH of about 7 is reached. The precipitate is filtered off with suction and thoroughly washed with water.

Yield: 1.12 g, $[\alpha]_D^{23} = -43.5°$ (c=1, methanol), decomposition above 168° C.

(1) Cyclo-(Aoc-Phe-D-Trp-Lys(Boc)-Val-Phe)

0.25 ml of ethylmethylphosphinic anhydride (50 percent), and slowly, with stirring, a solution of 0.4 ml of N-ethylmorpholine in 10 ml of dimethylformamide are added to a solution of 481.8 mg of H-D-Trp-Lys(Boc)-Val-Phe-Aoc-Phe-OH in 200 ml of dimethylformamide. After about two hours, the solution is evaporated and the residue is triturated with water. Yield: 0.5 g.

For purification, the product is chromatographed on silica gel in methylene chloride/methanol/water (1800: 280:20).

Yield: 200 mg.

(m) Cyclo-(Aoc-Phe-D-Trp-Lys-Val-Phe)

200 mg of cyclo-(Aoc-Phe-D-Trp-Lys(Boc)-Val-Phe) are dissolved in a mixture of trifluoroacetic acid/water 1,2-ethanedithiol (4.5 ml:0.5 ml:0.5 ml). The mixture is allowed to stand at room temperature for 90 minutes, then evaporated and the residue is partitioned between water and methyl tert.-butyl ether. The aqueous phase is adjusted to pH 3.6 with a weakly basic ion exchanger (acetate) and freeze-dried.

Yield: 126.7 mg.

Aminoacid analysis: (hydrolysis: 24 hours at 120° C. in 6N HCl): Val (0.97), Phe (2.05), Lys (1.00), Aoc (0.95) (content of peptide base: 81%).

Under these conditions, Trp is decomposed. A UV spectrum of the peptide shows the absorption at 277 nm characteristic of Trp.

EXAMPLE 7

Cyclo-(D-Trp-Lys-Thr-Phe-Aoc-Phe)

a. Boc-Aoc-Phe-OBzl 9.8 g of Boc-Aoc-OH, 11.2 g of HCl.H-Phe-OBzl, 5.2 g of HOBt and 4.9 ml of NEM were dissolved in 100 ml of DMF, 7.9 g of DCC were added and the mixture was stirred at room temperature for 14 hours. The precipitated DC-urea is filtered off with suction, the filtrate is evaporated in vacuo, the residue is taken up in 200 ml of ethyl acetate and the solution is extracted with citric acid and NaHCO$_3$ solution. An oily residue remains on evaporating the organic phase.

Yield: 20 g.

b. H-Aoc-Phe-OBzl.TFAcO 20 g of Boc compound from Example 7a are dissolved in 50 ml of trifluoroacetic acid. After 45 minutes, the mixture is evaporated in vacuo. An oil is again obtained. Yield: 22 g.

c. Boc-Phe-Aoc-Phe-OBzl 22 g of H-Aoc-Phe-OBzl.TFAcOH, 11.5 g of Boc-Phe-OH, 5.6 ml of NEM and 5.9 of HOBt were dissolved in 150 ml of ethyl acetate. After adding 9.0 g of DCC, reaction is allowed to continue at room temperature for 18 hours. The solid was filtered off with suction, and the organic phase was washed with citric acid and NaHCO$_3$ solution, dried over solid sodium sulfate, filtered and evaporated.

Yield: 22.4 g.

d. H-Phe-Aoc-Phe-OBzl.TFAcOH 22.4 g of Boc compound from Example 7c are dissolved in 50 ml of trifluoroacetic acid. After one hour, the mixture is evaporated at room temperature.

Yield: about 23 g.

e. Z-Lys(Boc)-Thr(tBu)-Phe-Aoc-Phe-Obzl 3.3 g of H-Phe-Aoc-OBzl.TFAcOH, 2.78 g of Z-Lys(Bov)-Thr(tBu)-OH, 0.7 g of HOBt and 0.7 ml of NEM are dissolved in 50 ml of ethyl acetate. After adding 1.07 g of DCC, reaction is allowed to continue overnight at RT. After extraction by shaking with citric acid and bicarbonate solution, the solution is dried and evaporated. The remaining brown oil is filtered through 400 g of silica gel (SiO$_2$-60, Merck AG) using the system CHCl$_3$ MeOH 13:1.

Yield: 5.1 g f. H-Lys(Boc)-Thr(tBu)-Phe-Aoc-Phe-OH 5 g of Z compound (Example 7e) are dissolved in 150 ml of methanol, and hydrogenation is carried out after adding 0.4 g of Pd/C (5% Pd). After absorption of hydrogen is complete, the mixture is filtered and the filtrate is evaporated in vacuo. The product is chromatographed on a silica gel column using the system CHCl$_3$/MeOH/HAcO 50:20:5.

Yield: 2.1 g. Two compounds are obtained, and the compound having the higher Rf value is reacted further.

g. Z-D-Trp-Lys(Boc)-Thr(tBu)-Phe-Aoc-Phe-OH 300 mg of H-Lys(Boc)-Thr(tBu)-Phe-Aoc-Phe-OH, 190 mg of Z-D-Trp-OTcp, 50 mg of HOBt and 50 μof NEM are dissolved in 10 ml of ethyl acetate and the solution is allowed to stand at room temperature for 48 hours. It is then evaporated and chromatographed on 150 g of silica gel (CHCl$_3$/MeOH 5:1).

Yield: 260 mg.

h. H-D-Trp-Lys(Boc)-Thr(tBu)-Phe-OH 260 mg of the Z derivative (Example 7g) are dissolved in 25 ml of MeOH, and 100 mg of Pd/C are added. After hydrogenation, the catalyst is filtered off and the filtrate is evaporated in vacuo.

Yield: about 240 mg.

i. Cyclo-(D-Trp-Lys(Boc)-Thr(tBu)-Phe-Aoc-Phe)

700 mg of linear peptide (Example 7h) are dissolved in 25 ml of DMF and, while stirring, 350 μl of ethylmethylphospinic anhydride and 0.1 ml of NEM are added. The reaction is allowed to continue overnight, then the mixture is evaporated in vacuo and the residue is chromatographed on 50 g of silica gel using the system $CH_2Cl_2$ $MeOH/H_2O$ 90:15:1.

Yield: 500 mg.

j. Cyclo-(D-Trp-Lys-Thr-Phe-Aoc-Phe)

500 mg of protected cyclo-hexapeptide (Example 7i) are dissolved in 5 ml of trifluoroacetic acid. After 45 minutes, the solution is evaporated in vacuo and precipitation with ether is carried out. The precipitate is taken up in a little ethanol and again precipitated with ether.

Yield: 450 mg.

Amionacid analysis: Lys=1.03; Phe=2.0; Thr=1.01; Aoc=0.99;

Content: 80%.

A and B are identical or different and denote alkyl having 1 to 3 carbon atoms, or A and B together represent a saturated, unsaturated or aromatic monocyclic or bicyclic structure having 3 to 6 carbon atoms, n denotes 0 or 1, and Y represents an aliphatic or aromatic L-aminoacid the side-chain of which can be hydroxylated, said amino acid being selected from the group consisting of L-alanine, L-serine, L-threonine, L-valine, L-leucine, L-isoleucine, L-phenylalanine, and L-tyrosine, and salts thereof with physiologically tolerated acids.

2. A compound of the formula III as claimed in claim 1 in which Y represents threonine.

3. A compound of the formula III as claimed in claim 1, in which X represents the radical of tetrahydroisoquinoline-3-L-carboxylic acid.

4. A compound of the formula III as claimed in claim 1, in which X represents the radical of cis,endooctahydro-[1H]-indole-2-L-carboxylic acid.

5. A compound of the formula III as claimed in claim 1, in which X represents the radical of cis,endooctahdrocyclopenta[b]pyrrole-2-L-carboxylic acid.

6. A cyclic hexapeptide of the formula III

Example 7, diagram of synthesis

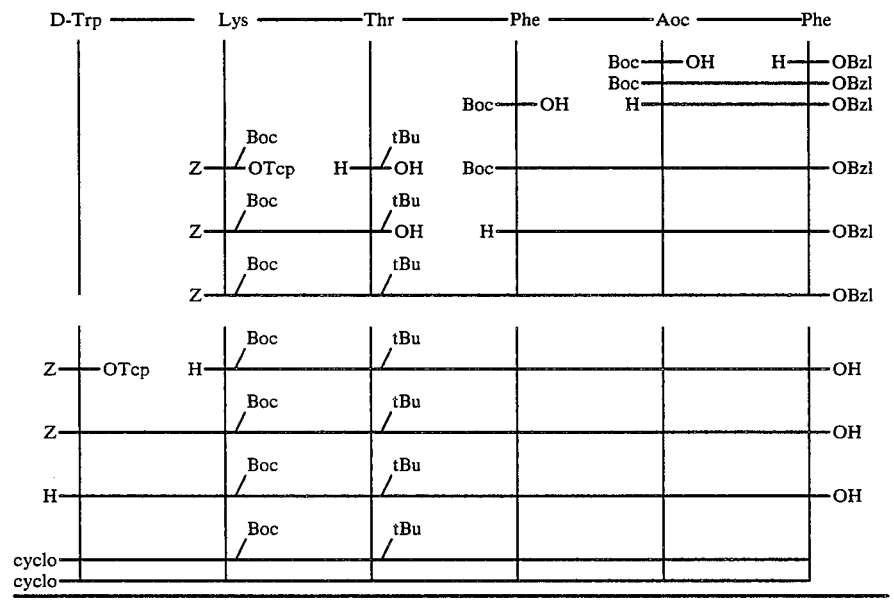

We claim:

1. A cyclic hexapeptide of the formula III

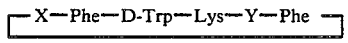

in which X represents the radical of an L-aminoacid of the formula IIIa

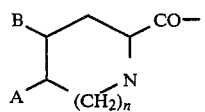

in which

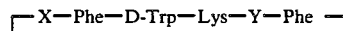

in which X represents the radical of a bicyclic L-aminoacid selected from the group consisting of tetrahydroisoquinoline-3-carboxylic acid; decahydroisoquinole-3-carboxylic acid; 2,3-dihydro-[1H]-indole-2-carboxylic acid; cis,exo-octahydro[1H]-indole-2-carboxylic acid; cis,exo-octahydro-2-cyclopenta[b]-pyrrole-2-carboxylic acid; cis,exo-aza-bicyclo[5.3.0]-decane-3-carboxylic acid; cis,endo-octahydrocyclopenta[b]-pyrrole-2-carboxylic acid; cis,endo-azabicyclo-[5.3.0]decane-3-carboxylic acid; cis,endo-2,3,3a,4,5,7a-hexahydro-[1H]indole-2-carboxylic acid; cis,exo- 2,3,3a,4,5,7a-hexahydro-[H]indole-2-carboxylic acid; and cis,endo-octahydro-[1H]-indole-2-carboxylic acid;

Y denotes a radical of an aminoacid selected from the group consisting of L-alanine, L-serine, L-threonine, L-valine, L-leucine, L-isoleucine, L-phenylalanine, and L-tyrosine;

and salts thereof with physiologically tolerated acids.

7. A compound as claimed in claim 1 having the formula

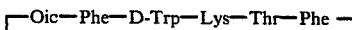

8. A compound as claimed in claim 1 having the formula

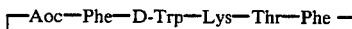

9. A compound as claimed in claim 1 having the formula

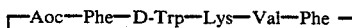

10. A compound as claimed in claim 1 having the formula

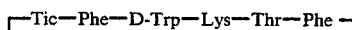

11. A pharmaceutical composition comprising a compound as claimed in claim 1 or a pharmaceutically acceptable salt thereof and a pharmaceutically acceptable carrier, said compound being present in an amount effective to treat hemmorhage of the gastrointestinal tract, metabolic disturbances associated with raised levels of hormones which can be inhibited by somatostatin, gastric ulcers, acromegaly, psoriasis, or diabetes mellitus.

12. A process for inhibiting gastric acid secretion by administering an effective amount of a compound as claimed in claim 1 or a pharmaceutically acceptable salt thereof.

13. A process for the treatment of hemorrhage of the gastrointestinal tract by administering an effective amount of a compound as claimed in claim 1 or a pharmaceutically acceptable salt thereof.

14. A process for treating metabolic disturbances associated with raised levels of hormones which can be inhibited by somatostatin by administering an effective amount of a compound as claimed in claim 1 or a pharmaceutically acceptable salt thereof.

15. A process for the treatment of gastric ulcers by administering an effective amount of a compound as claimed in claim 1 or a pharmaceutically acceptable salt thereof.

16. A process for the treatment of acromegaly by administering an effective amount of a compound as claimed in claim 1 or a pharmaceutically acceptable salt thereof.

17. A process for the treatment of psoriasis by administering an effective amount of a compound as claimed in claim 1 or a pharmaceutically acceptable salt thereof.

18. A process for treating diabetes mellitus by administering an effective amount of a compound as claimed in claim 1 or a pharmaceutically acceptable salt thereof.

19. A process for treating metabolic disturbances in which insulin and growth hormone in the plasma are too high by administering an effective amount of a compound as claimed in claim 1 or a pharmaceutically acceptable salt thereof.

* * * * *